United States Patent [19]

Bedford

[11] 4,082,511
[45] Apr. 4, 1978

[54] METHOD FOR PROTECTING AN INTERNAL COMBUSTION ENGINE BY DETERMINING THE CHANGE POINT OF THE LUBRICATION OIL

[75] Inventor: John E. Bedford, Houston, Tex.

[73] Assignee: Pricon, Inc., Tex.

[21] Appl. No.: 722,084

[22] Filed: Sep. 10, 1976

[51] Int. Cl.² .......................................... G01N 33/30
[52] U.S. Cl. .......................... 23/230 HC; 23/230 R; 73/64
[58] Field of Search ...................... 23/230 HC, 230 M; 73/15, 61, 64; 324/61

[56] References Cited

U.S. PATENT DOCUMENTS

| | | | |
|---|---|---|---|
| 2,486,080 | 10/1949 | Turner et al. | 73/64 |
| 2,669,865 | 2/1954 | Cole et al. | 73/64 |
| 3,182,255 | 5/1965 | Hopkins et al. | 324/61 |
| 3,274,820 | 9/1966 | Komarmy | 73/61 |
| 3,653,838 | 4/1972 | Glass | 23/230 HC |
| 3,811,837 | 5/1974 | Hoffman et al. | 23/230 HC |
| 3,968,677 | 7/1976 | Felton et al. | 73/15 |

OTHER PUBLICATIONS

1972 Annual Book of ASTM Standards, Part 17, pp. 227-234.
Fisher Scientific Company, TD-164, Technical Data, Dec. 1962, pp. 1-12.
Orion Research, Instruction Manual model 407A, Orion Research Inc., Form IM407A/4701, © 1974, pp. 1-18.

*Primary Examiner*—R.E. Serwin
*Attorney, Agent, or Firm*—Pravel, Wilson & Gambrell

[57] ABSTRACT

A new and improved on-site method for protecting an internal combustion engine in the field for maximizing service time by determining the change point of the lubrication oil when the TBN declines to a predetermined level. The on-site method utilizes a new field system fitted in a portable carrying case or a small cabinet and containing all the equipment necessary for analyzing lubrication oil including predetermined indicator marks on equipment for simplicity of application and for facilitating use by unskilled operators. The method includes two steps of titrating samples of lubrication oil for obtaining the TBN and TAN to indicate the change point of the lubricating oil when the TBN declines to a predetermined minimum. The method also can indicate a predicted change point so downtime for engine servicing can be scheduled. The TAN serves as an indicator of the amount of acid build-up in the lubrication oil.

17 Claims, 4 Drawing Figures

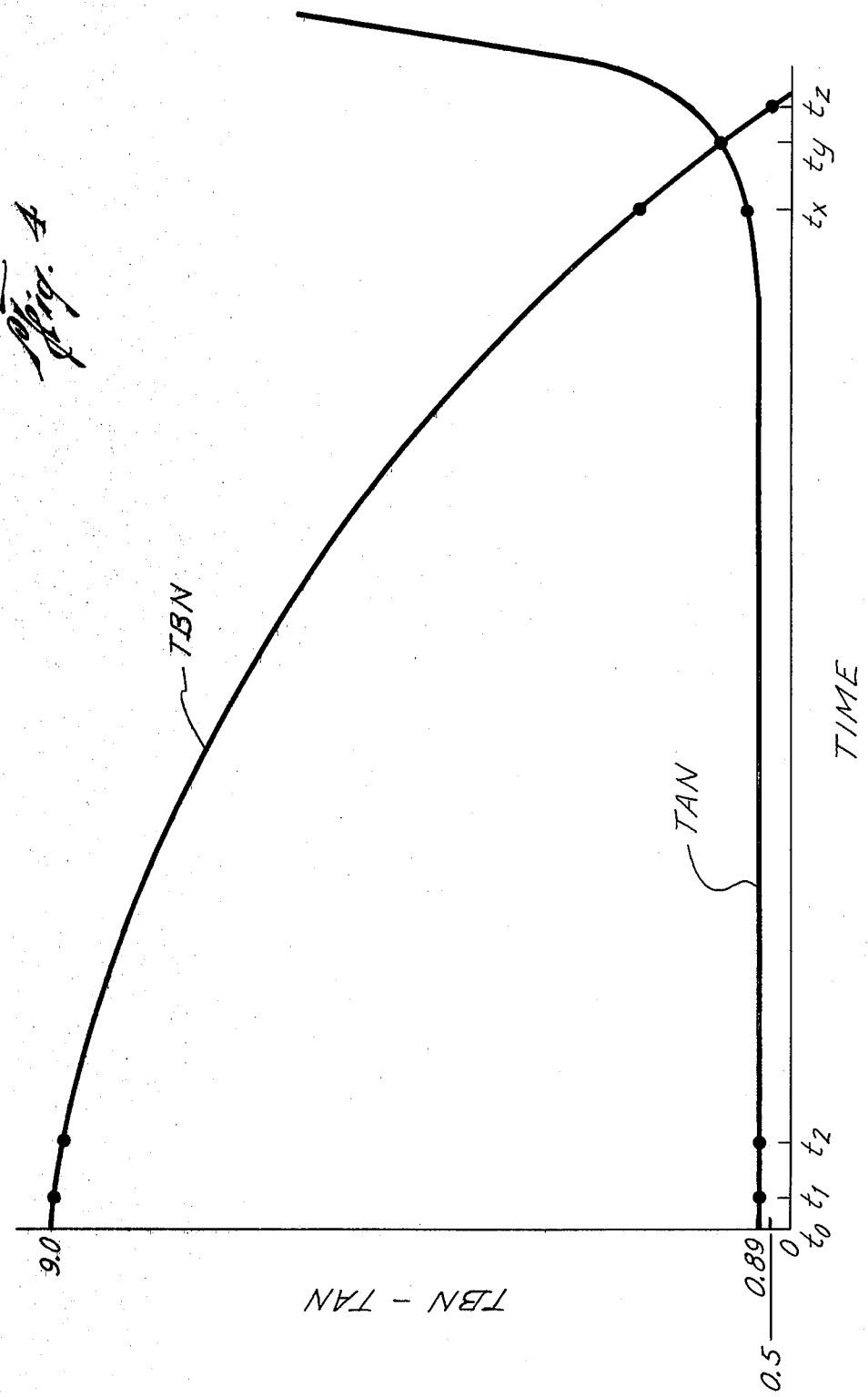

METHOD FOR PROTECTING AN INTERNAL COMBUSTION ENGINE BY DETERMINING THE CHANGE POINT OF THE LUBRICATION OIL

BACKGOUND OF THE INVENTION

This invention relates generally to the field of protecting an internal combustion engine by determining when an oil change is required.

The acidity of lubricating oil in internal combustion engines is generally believed to be detrimental to the operating life of an engine. Accordingly, manufacturers' recommended service time for oil changes generally take into consideration a substantial safety factor to insure that the relative acidity of the oil is maintained below a certain level. This may result in premature frequent oil changes, particularly when a high sulfur content fuel is used and due to the unavailability of an on-site in the field system and method for analyzing the engine oil. When the fuel sulfur content is greater than one percent, then the recommended service time may be reduced by a factor by as much as four. If the fuel sulfur content is greater than one percent and no corrective action is taken, then the life span of an engine may be reduced by as much as fifty percent. Large internal combustion engines may have a lubricating oil capacity of as much as 165 gallons or greater and the recommended service time based on the estimated sulfuric acid build-up in the oil may be in the order of a few hundred hours. In the case of marine applications and remote field locations, maximizing the time between oil changes by determining the precise change point may provide substantial savings in the cost of the oil, storage and transportation in addition to providing lubrication protection to the engine.

An alternative to simply changing the oil at estimated safe intervals is to test the oil regularly and change whenever the test indicates a change is necessary. So far as known, the usual prior art method for testing the lubrication oil of an internal combustion engine has consisted of obtaining a sample of the oil and transporting this sample to a laboratory for analysis. Otherwise, change time has been arbitrarily set at a predetermined point based on engine manufacturers' recommendations. While such a method can correctly analyze the engine oil to determine numerous art recognized factors, such as flash point, pour point, ppm of wear metals, viscosity, sulfated ash content, TBN and TAN, the time delays involved in obtaining results make this method unsatisfactory for determining oil change times, particularly when the internal combustion engine is located at a remote location from a laboratory. It has been known that TAN and TBN could be determined by titrating with a basic solution and an acid solution, respectively. One such method for such determining of TAN and TBN is set forth in ASTM D-664-54 (reapproved 1968). There is no known acceptable field system which has been available on the market to provide reliable protection of an engine by testing of lubrication oil on-site in the field for immediate determination of the useful life of a lubrication oil. Known U.S. patents relating to testing lubrication oils are Nos. 2,486,080; 2,669,865; 3,182,255; 3,274,820; 3,653,838; 3,811,837; and 3,968,677.

SUMMARY OF THE INVENTION

This invention relates to a new and improved method for protecting an internal combustion engine by determining the change point of the engine oil of the engine. The method includes the use of a portable system which can be fitted into a relatively small storage or carrying case for transporting and using on the job at remote locations. The method includes the steps of withdrawing samples of lubricating oil from an internal combustion engine crankcase and titrating each samples of engine oil with different titrating solutions to obtain the TBN (total base number) and to obtain the TAN (total acid number) and then using these values as the criteria for precisely determining the change point for maximizing operating time while detecting an acid build-up which could be harmful to an engine. The system includes the use of predetermined indicators on the components of the system so that the method can readily be practiced without any special training or knowledge on the part of the operator. Also, the method can be used as a basis to determine in the field whether or not a lubricating oil is the wrong type for the engine, based on percent sulfur in fuel being burned. With the practice of this method, mere guesswork is not involved in determining the precise change point for a lubricating oil. Periodic testing with the method permits advance scheduling of downtime for engine servicing.

BRIEF DESCRIPTION OF THE DRAWINGS

FIG. 4 is a diagrammatic graph showing the TBN and TAN plotted at test invervals.

DESCRIPTION OF THE PREFERRED EMBODIMENT

Figure 1:
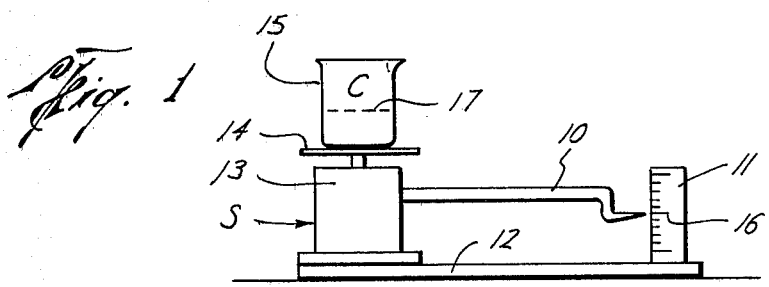
FIG. 1 is an elevation view of a portable scale and the first container for a sample of lubrication oil.
Figure 2:
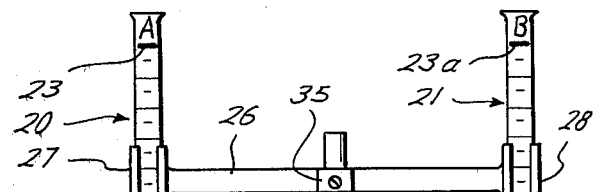
FIG. 2 is an elevation view of a portion of the system for testing a sample of lubrication oil.
Figure 2:
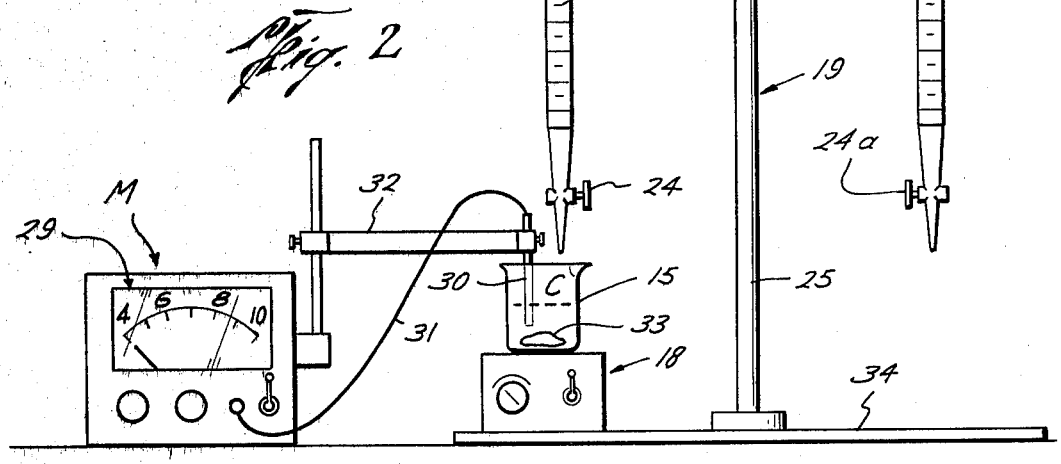
Figure 3:
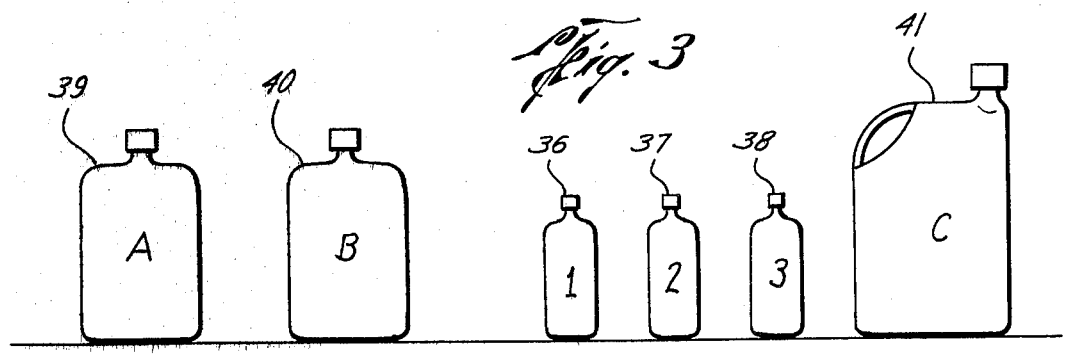
FIG. 3 is an elevation view of the reagents used to test a sample of lubrication oil.

A system for performing the method steps of the new and improved method for protecting an engine by testing a lubrication oil is shown in FIGS. 1-3 of the drawings. As shown in FIG. 1, the system includes a scale S which is schematically shown having a pointer 10 whose relative position is read on the calibration scale 11. The scale includes a base member 12 to which is attached the weighing mechanism 13 having a platform 14. The scale S preferably has a triple beam balance with a tare adjustment which compensates for the weight of the first container 15. It is understood that any type of scale could be used which would provide accurate measurements and which would be small enough to be suitably portable. The schematic illustration of the scale shows a zero mark 16 which is used in determining the amount of lubrication added to the first container 15.

The first container or beaker 15 is labeled with the letter C and also includes a predetermined indicator mark 17 which in the preferred embodiment indicates when 125 ml has been added to container 15. The sole indicator mark 17 facilitates use of this system by an unskilled operator since the directions for following the method need only indicate that solution C be added to the container 15 to the indicator mark. This is of particular importance since the system and method of this invention has particular utility for on-site in the field use where a skilled laboratory technician may be unavailable.

The testing apparatus of this invention is best shown in FIG. 2 of the drawing. The apparatus includes a pH meter M, a magnetic stirrer 18 and a dual burette holder 19 supporting burettes 20 and 21. Burettes 20 and 21 are identical in construction and are plainly marked with the letters A and B for a reason as explained hereinafter. Burette 20 includes a cylindrical calibrated portion having calibration marks 22 which begin with a zero indicator mark 23 which tells an operator the amount of titrating solution which is added to each burette. A standard valve 24 is provided for releasing small quantitites of the titrating solution at selective intervals during the step of titrating. The burette 21 includes a zero indicator mark 23a, calibration marks 22a and valve 24a. The dual burette holder 19 includes a central post 25 with a cross member 26 secured thereto. The cross member 26 includes identical releasable clamps 27 and 28 for releasable holding the burettes 20 and 21, respectively. The central post 25 is secured to a base member 34 which in turn provides a support for the magnetic stirrer 18. The cross member 26 may be mounted for rotation about the support post 25 with the connector 35 so that the cross member 26 may be rotated to selectively position burette 20 or burette 21 over the magnetic stirring base 18.

The pH meter M is of the conventional type which includes a calibrated scale 29 for observing pH readings. The pH meter may be battery powered to allow its operation where an auxiliary power supply is not readily available or may be electrically powered from an outlet. An electrode 30 is connected to the pH meter M through a conductor wire 31. The electrode 30 is mounted in an adjustable support 32 which is adapted to be attached to the pH meter M. It is understood that the electrode 30 when inserted in a solution in the first container 15 transmits a signal to the pH meter M which is converted to a reading on the scale 29 for determining the pH of the solution in the container 15. A variable speed magnetic stirrer 18 is provided to cause rotation of a stirring bar 33 which is positioned in the container 15. The magnetic stirrer 15 provides agitation to the solution in the first container 15 to thoroughly mix the solution therein particularly during the titrating operation to provide an accurate reading of the pH of the solution.

FIG. 3 illustrates the reagents used in testing a sample of lubricating fluid using the method of this invention. Small containers 36, 37 and 38 are labeled with the numbers 1, 2 and 3 for identification by an operator. These small containers are used for three buffer solutions which, for example, may have a pH of 4, 7 and 10, respectively. The solutions in these containers are used for accurately calibrating the pH meter M before performing the titration steps of this invention. The numbering of these small containers provide easy identification by an operator when following the directions for the method of this invention.

Second and third storage containers or bottles 39 and 40 are provided for the titrating reagents used in the method of this invention. These two storage containers or bottles are labeled with the large letters A and B to provide for identification by the operator in performing the method of this invention. These containers are used for the two titrating solutions which, in the case of this invention, are 0.1 N KOH alcoholic in bottle 39 and 0.1 N HCl alcoholic in bottle 40. The letter A on the bottle 39 corresponds to the letter A on the burette 20 so that the operator will not confuse the reagents used in the method of this invention, i.e., TAN = bottle A and burette A. Fourth storage container 41 is labeled with the letter C and contains a titration solvent as further described hereinafter.

Aside from cleaning materials, such as a wash bottle and the like and the written directions and charts, the above described components of the system substantially constitute the entire system which is used to provide an accurate testing of lubrication oil in an internal combustion engine for determining the precise change point as well as predict the change point. The components of this system are designed to be placed in a portable carrying case or a small cabinet which is located in the field with the internal combustion engine. This is possible because of the relatively small number of components including reagents which provide sufficient information to make a determination as to the proper time to change the engine oil. The labeling of the components with predetermined indicator marks simplifies the operation in the method of this invention so that the method may be carried out with a minimum amount of training on the part of the operator. Additional containers, like container 15, and also labeled C, may be included in a system to allow monitoring of several engines at a field site.

Method steps of this invention can be readily understood with reference to FIGS. 1–3. An initial step in the method of this invention includes removing the components of this invention from the carrying or storage case. The container 15 which is labeled C is positioned on the scale S as shown in FIG. 1. A first amount of lubrication oil is withdrawn from the crankcase of an internal combustion engine and is added to the container 15 labeled C until the scale indicator 10 indicates that in the order of 5 grams of lubrication oil has been added to the container 15. For example, the 5 grams of lubrication oil may be about 7 to 8 drops added to the container 15.

After the addition of the predetermined amount of lubrication oil from the crankcase to the container 15, titration solvent from the storage container 41 is added to the container 15 up to the predetermined indicator mark 17 which is at the 125 ml point. the titration solvent preferably contains in the order of 500 ml of isopropyl alcohol, 495 ml toluene and 5 ml of distilled water per liter of titration solvent. It is understood that the container 15 is removed from the scale S before the addition of the titration solvent.

The titration solution from storage container 39 labeled A is added to the burette labeled A until the solution reaches the zero indicator mark 23. The titration solution from storage container 40 labeled B is added to the burette labeled B to a similar zero indicator mark, i.e., TBN = bottle B and burette B. The container 15 may be then positioned on the magnetic stirrer 18 and the stirrer bar 33 may be inserted in the solution containing the test sample of lubricating oil and the titration solvent which is positioned underneath the burette labeled A. Releasable electrode supporting clamp can be positioned on the container labeled C to position the electrode 30 in the test solution. The magnetic stirrer 18 may then be turned on to agitate the test solution to provide an accurate reading on the pH meter.

It is understood that the pH meter is calibrated using the buffer solutions and the small containers labeled 1, 2 and 3 so that an accurate reading can be obtained on the pH meter. The system of this invention as shown in FIG. 2 is set up for the testing procedure which provides for a determination of the change point of the lubricating fluid.

After filling the burettes 20, labeled A and B, and positioning the container 15 as shown in FIG. 2, the steps of titrating the test solution may be commenced. The control valve 24 is used to add an undetermined amount of solution A to the test solution in the container 15 to decrease the pH of the test solution to a predetermined pH number which is preferably 11. The amount of titrating solution A which is used is then readily determinable by reading the calibrated scale on the burette 20 which indicates the number of ml used. An operator then goes to the following chart which includes calculations for the TAN based on the ml of titrating solution used:

CONVERSION CHART

| ml Added | TBN/TAN | ml Added | TBN/TAN | ml Added | TBN/TAN |
|---|---|---|---|---|---|
| 0.1 | = 0.112 | 5.4 | = 6.058 | 10.7 | = 12.005 |
| 0.2 | = 0.224 | 5.5 | = 6.171 | 10.8 | = 12.117 |
| 0.3 | = 0.336 | 5.6 | = 6.283 | 10.9 | = 12.229 |
| 0.4 | = 0.448 | 5.7 | = 6.395 | 11.0 | = 12.342 |
| 0.5 | = 0.561 | 5.8 | = 6.507 | 11.1 | = 12.454 |
| 0.6 | = 0.673 | 5.9 | = 6.619 | 11.2 | = 12.566 |
| 0.7 | = 0.785 | 6.0 | = 6.732 | 11.3 | = 12.678 |
| 0.8 | = 0.897 | 6.1 | = 6.844 | 11.4 | = 12.790 |
| 0.9 | = 1.009 | 6.2 | = 6.956 | 11.5 | = 12.903 |
| 1.0 | = 1.122 | 6.3 | = 7.068 | 11.6 | = 13.015 |
| 1.1 | = 1.234 | 6.4 | = 7.180 | 11.7 | = 13.127 |
| 1.2 | = 1.346 | 6.5 | = 7.293 | 11.8 | = 13.239 |
| 1.3 | = 1.458 | 6.6 | = 7.405 | 11.9 | = 13.351 |
| 1.4 | = 1.570 | 6.7 | = 7.517 | 12.0 | = 13.464 |
| 1.5 | = 1.683 | 6.8 | = 7.629 | 12.1 | = 13.576 |
| 1.6 | = 1.795 | 6.9 | = 7.741 | 12.2 | = 13.688 |
| 1.7 | = 1.907 | 7.0 | = 7.854 | 12.3 | = 13.800 |
| 1.8 | = 2.019 | 7.1 | = 7.966 | 12.4 | = 13.912 |
| 1.9 | = 2.131 | 7.2 | = 8.078 | 12.5 | = 14.025 |
| 2.0 | = 2.244 | 7.3 | = 8.190 | 12.6 | = 14.137 |
| 2.1 | = 2.356 | 7.4 | = 8.302 | 12.7 | = 14.249 |
| 2.2 | = 2.468 | 7.5 | = 8.415 | 12.8 | = 14.361 |
| 2.3 | = 2.580 | 7.6 | = 8.527 | 12.9 | = 14.473 |
| 2.4 | = 2.692 | 7.7 | = 8.639 | 13.0 | = 14.586 |
| 2.5 | = 2.805 | 7.8 | = 8.751 | 13.1 | = 14.698 |
| 2.6 | = 2.917 | 7.9 | = 8.863 | 13.2 | = 14.810 |
| 2.7 | = 3.029 | 8.0 | = 8.976 | 13.3 | = 14.922 |
| 2.8 | = 3.141 | 8.1 | = 9.088 | 13.4 | = 15.034 |
| 2.9 | = 3.253 | 8.2 | = 9.200 | 13.5 | = 15.147 |
| 3.0 | = 3.366 | 8.3 | = 9.312 | 13.6 | = 15.259 |
| 3.1 | = 3.478 | 8.4 | = 9.424 | 13.7 | = 15.371 |
| 3.2 | = 3.590 | 8.5 | = 9.537 | 13.8 | = 15.483 |
| 3.3 | = 3.702 | 8.6 | = 9.699 | 13.9 | = 15.595 |
| 3.4 | = 3.814 | 8.7 | = 9.761 | 14.0 | = 15.708 |
| 3.5 | = 3.927 | 8.8 | = 9.873 | 14.1 | = 15.820 |
| 3.6 | = 4.039 | 8.9 | = 9.985 | 14.2 | = 15.932 |
| 3.7 | = 4.151 | 9.0 | = 10.098 | 14.3 | = 16.044 |
| 3.8 | = 4.263 | 9.1 | = 10.210 | 14.4 | = 16.156 |
| 3.9 | = 4.375 | 9.2 | = 10.322 | 14.5 | = 16.269 |
| 4.0 | = 4.488 | 9.3 | = 10.434 | 14.6 | = 16.381 |
| 4.1 | = 4.600 | 9.4 | = 10.546 | 14.7 | = 16.493 |
| 4.2 | = 4.712 | 9.5 | = 10.659 | 14.8 | = 16.605 |
| 4.3 | = 4.824 | 9.6 | = 10.771 | 14.9 | = 16.717 |
| 4.4 | = 4.936 | 9.7 | = 10.883 | 15.0 | = 16.830 |
| 4.5 | = 5.049 | 9.8 | = 10.995 | 15.1 | = 16.942 |
| 4.6 | = 5.161 | 9.9 | = 11.107 | 15.2 | = 17.054 |
| 4.7 | = 5.273 | 10.0 | = 11.220 | 15.3 | = 17.166 |
| 4.8 | = 5.385 | 10.1 | = 11.332 | 15.4 | = 17.278 |
| 4.9 | = 5.497 | 10.2 | = 11.444 | 15.5 | = 17.391 |
| 5.0 | = 5.610 | 10.3 | = 11.556 | 15.6 | = 17.503 |
| 5.1 | = 5.722 | 10.4 | = 11.668 | 15.7 | = 17.615 |
| 5.2 | = 5.834 | 10.5 | =S 11.781 | 15.8 | = 17.727 |
| 5.3 | = 5.946 | 10.6 | = 11.893 | 15.9 | = 17.839 |
| 16.0 | = 17.592 | 21.3 | = 23.898 | | |
| 16.1 | = 18.064 | 21.4 | = 24.010 | | |
| 16.2 | = 18.176 | 21.5 | = 24.123 | | |
| 16.3 | = 18.288 | 21.6 | = 24.235 | | |
| 16.4 | = 18.400 | 21.7 | = 24.347 | | |
| 16.5 | = 18.513 | 21.8 | = 24.459 | | |
| 16.6 | = 18.625 | 21.9 | = 24.571 | | |
| 16.7 | = 18.737 | 22.0 | = 24.684 | | |
| 16.8 | = 18.849 | 22.1 | = 24.796 | | |
| 16.9 | = 18.961 | 22.2 | = 24.908 | | |
| 17.0 | = 19.074 | 22.3 | = 25.020 | | |
| 17.1 | = 19.186 | 22.4 | = 25.132 | | |
| 17.2 | = 19.298 | 22.5 | = 25.245 | | |
| 17.3 | = 19.410 | 22.6 | = 25.357 | | |
| 17.4 | = 19.522 | 22.7 | = 25.469 | | |
| 17.5 | = 19.635 | 22.8 | = 25.581 | | |
| 17.6 | = 19.747 | 22.9 | = 25.693 | | |
| 17.7 | = 19.859 | 23.0 | = 25.806 | | |
| 17.8 | = 19.971 | 23.1 | = 25.918 | | |

-continued

CONVERSION CHART

| ml Added | TBN/TAN | ml Added | TBN/TAN | ml Added | TBN/TAN |
|---|---|---|---|---|---|
| 17.9 | = 20.083 | 23.2 | = 26.030 | | |
| 18.0 | = 20.196 | 23.3 | = 26.142 | | |
| 18.1 | = 20.308 | 23.4 | = 26.254 | | |
| 18.2 | = 20.420 | 23.5 | = 26.367 | | |
| 18.3 | = 20.532 | 23.6 | = 26.479 | | |
| 18.4 | = 20.644 | 23.7 | = 26.591 | | |
| 18.5 | = 20.757 | 23.8 | = 26.703 | | |
| 18.6 | = 20.869 | 23.9 | = 26.815 | | |
| 18.7 | = 20.981 | 24.0 | = 26.928 | | |
| 18.8 | = 21.093 | 24.1 | = 27.040 | | |
| 18.9 | = 21.205 | 24.2 | = 27.152 | | |
| 19.0 | = 21.318 | 24.3 | = 27.264 | | |
| 19.1 | = 21.430 | 24.4 | = 27.376 | | |
| 19.2 | = 21.542 | 24.5 | = 27.489 | | |
| 19.3 | = 21.654 | 24.6 | = 27.601 | | |
| 19.4 | = 21.766 | 24.7 | = 27.713 | | |
| 19.5 | = 21.879 | 24.8 | = 27.825 | | |
| 19.6 | = 21.991 | 24.9 | = 27.937 | | |
| 19.7 | = 22.103 | 25.0 | = 28.050 | | |
| 19.8 | = 22.215 | | | | |
| 19.9 | = 22.327 | | | | |
| 20.0 | = 22.440 | | | | |
| 20.1 | = 22.552 | | | | |
| 20.2 | = 22.664 | | | | |
| 20.3 | = 22.776 | | | | |
| 20.4 | = 22.888 | | | | |
| 20.5 | = 23.001 | | | | |
| 20.6 | = 23.113 | | | | |
| 20.7 | = 23.225 | | | | |
| 20.8 | = 23.337 | | | | |
| 20.9 | = 23.449 | | | | |
| 21.0 | = 23.562 | | | | |
| 21.1 | = 23.674 | | | | |
| 21.2 | = 23.786 | | | | |

For example, assuming 1.0 ml of solution A was used, the above calculations in the chart would indicate a TAN of 1.009 which is accurate to in the order of about 0.001. The TAN indicates the amount of acid build-up.

The procedure for determining the TBN includes measuring an additional predetermined amount of lubrication oil from an engine crankcase which may be in the order of 5 g. This predetermined amount of oil is weighed on the scale as noted above after first cleaning the container 15 or obtaining another clean container 15. Titration solvent is added to the container 15 to bring the level to the predetermined indicator mark and the container is positioned on the magnetic stirrer base and a stirrer bar inserted therein.

The burette 21, labeled B, may then be positioned over the container 15 for titration of the test solution with the titration solution B. The titration solution B, 0.1 N HCl alcoholic, has been added to the burette 21, labeled B, from the container 40, labeled B, until the zero mark 23a on the burette 21 is reached. The solution B may then be added to the test solution with the valve 24a until the pH in the solution declines to a predetermined value which may be 4. The amount of titrating solution B can be readily determined from the scale 22a for determining the TBN. The TBN is determined from the above chart by locating the number of ml of 0.1 N HCl alcoholic added which corresponds to a certain TBN value. For example, assuming 2.6 ml of solution B was used, the above calculations in the chart would indicate a TBN of 2.917 which is accurate in order of about 0.001. The greater the amount of solution A is needed to reach a pH of 4 on the scale of the pH meter, the greater the time until the change point of the oil. This relatively accurate, safe, reliable method for determining the change point for lubrication oil provides for a maximum utilization of the lubrication oil. The change time for changing the oil is when the alkaline reserve is depleted to the point when the TBN falls to a value of from about 1.0 to 0.5. In other words, the TBN is not allowed to go below about 0.5 to protect the engine from potential acid damage caused by total depletion of the oil alkaline reserve. This TBN value of about 0.5 is considered the critical point for the oil change time because at about this point the TBN drops very rapidly to zero for most oils. Changing the oil when the TBN is greater than 1.0, absent other determining factors, is considered as wasting of good oil. When the alkaline additive has been neutralized, a rapid acid build-up commences.

An example of an engine oil used in large diesel power plants is Mobil (trademark) Delvac 1340. The specifications for new Mobil Delvac 1340 oil may indicate an initial TBN of 9.0 and an initial TAN of .89. Using the above method of this invention, it is possible to plot the TBN versus time, as shown in FIG. 4, to predict the change point so downtime for engine servicing could be scheduled. For instance, the TBN is plotted on the vertical axis versus time plotted on the horizontal axis corresponding to periodic testing of the lubrication oil. The TAN curve begins, as shown in FIG. 4, at 0.89 on the scale and slopes gradually upwardly with the use or wear (oxidation) of the lubricating oil.

In FIG. 4, the curve for TBN begins at 9.0 in this example when new oil has been added to the engine ($t_o$). Tests are performed at periodic intervals ($t_1$, $t_2$) to obtain values for the TBN and TAN. Once several tests are made, it is possible to determine the frequency of tests. For instance, as the operating hours between oil changes increase ($t_x$), the frequency of testing may increase. In the beginning, tests may, for instance, be made at three day intervals. The test intervals may be reduced to one day as the operating hours on the oil increase. The frequency of testing will generally depend on the fuel sulfur content as well as other factors. At time $t_y$ the TBN curve crosses the TAN curve. The change point of general oils (TBN = 0.5) occurs at about $t_z$. At about this point, the TBN drops off rapidly to zero and the TAN begins a rapid rise as indicated. Accordingly, it is important to closely monitor an engine when the TBN approaches about 0.5 because of the rapid drop of TBN and rapid rise of TAN. The change point may vary with different types of oil depending on the characteristics of the oil. If for some reason it is not practical or impossible to change the oil at time $t_z$, then the test is continued to indicate the TAN value. The greater the TAN value, the greater the chances of damaging the engine. While the TBN is the determining factor in indicating the change point, it is preferably to also determine the TAN during testing as a further indication of the acid build-up.

When the TBN is determined to be about 0.5, it is important to change the lubrication oil in the engine since further build-up of acid in the crankcase could result in unnecessary damage to the engine, such as pitting of the bearing surfaces. The above-described method provides an accurate on-site in the field determination of the TBN which can be safely used by a relatively unskilled operator without any guesswork in determining the maximum utilization of the lubrication oil.

The foregoing disclosure and description of the invention are illustrative and explanatory thereof, and various changes in the size, shape and materials as well as in the details of the illustrated construction, may be made without departing from the spirit of the invention.

I claim:

1. An on-site method for protecting an internal combustion engine by precisely determining the change point for the lubricating oil of the engine in the field for maximum utilization of the oil and for preventing damage to the engine, comprising the steps of:
   measuring a predetermined amount of lubrication oil withdrawn from an internal combustion engine at the site in the field;
   diluting the predetermined amount of lubrication oil with a predetermined amount of titration solvent;
   titrating the predetermined amount of diluted lubrication oil at the site in the field with an amount of a first premixed titrating solution sufficient to reduce the pH level of the lubrication oil to a first predetermined value;
   determining the Total Base Number at the site in the field from the measured amount of the first titrating solution; and
   changing the lubricating oil when the Total Base Number declines to a value of from about 1.0 to 0.5.

2. The method as set forth in claim 1, wherein:
   the step of titrating with the first titrating solution includes adding increments of 0.1 N HCl alcoholic at intervals until the pH of the predetermined amount of lubrication oil has declined to the first predetermined value.

3. The method as set forth in claim 1, wherein:
   the step of measuring a predetermined amount of lubrication oil at the site in the field includes determining the predetermined amount by weight on a portable scale.

4. The method as set forth in claim 1, including the steps of:
   measuring an additional predetermined amount of lubrication oil withdrawn from the internal combustion engine at the site in the field;
   diluting the predetermined amount of lubrication oil with a predetermined amount of the titration solvent;
   titrating the additional predetermined amount of diluted lubrication oil at the site in the field with an amount of a second premixed titrating solution sufficient to increase the pH level to a second predetermined value; and
   determining the Total Acid Number at the site in the field from the measured amount of the second titrating solution.

5. The method as set forth in claim 4, wherein the step of titrating with the second titration solution includes:
   adding increments of 0.1 N KOH alcoholic at intervals until the pH of the second predetermined amount of lubrication oil has increased to the second predetermined value.

6. An on-site method for protecting an internal combustion engine by precisely determining the change point for the lubricating oil of the engine in the field and for preventing damage to the engine, comprising the steps of:
   adding in the order of five grams of lubricating oil from the engine crankcase on-site in the field to a first container as determined by a portable scale preset for the container;
   pouring in the order of 125 ml premixed titration solvent from a first storage container up to a predetermined mark on the first container;

inserting a magnetic stirrer in the first container and positioning the first container on a magnetic stirrer base for providing agitation of the solution in the first container;

installing an electrode of a portable pH meter in the first container for measuring the pH of the solution in the first container;

pouring in the order of 25 ml of 0.1 n HC1 alcoholic from a second container to a predetermined zero mark of a first burette;

titrating the solution in the first container with the first burette to lower the pH of the solution to in the order of 4 on the pH meter;

reading the first burette to determine the volume of 0.1 N HC1 alcoholic used;

determining the Total Base Number from the volume of 0.1 N HC1 alcoholic used; and changing the lubrication oil when the Total Base Number has declined to a value of from about 1.0 to 0.5.

7. The method as set forth in claim 6, including the step of:

calibrating the pH meter prior to the step of titrating with three buffers in fourth, fifth and sixth containers and having predetermined pH values of in the order of 4, 7 and 10.

8. The method as set forth in claim 1, including the step of:

adding a predetermined amount of premixed titration solvent comprising in the order of 495 ml toluene, 500 ml isopropyl alcohol, 5 ml distilled water per liter of solvent to the predetermined amount of lubricating oil at the site in the field before performing the titration.

9. The method as set forth in claim 6, wherein the step of adding the premixed titration solvent includes:

adding a premixed solvent comprising in the order of 495 ml toluene, 500 ml isopropyl alcohol and 5 ml distilled water per liter of solvent.

10. The method as set forth in claim 6, including the steps of:

adding in the order of an additional 5 g of lubricating oil from the engine crankcase on-site in the field to a second container as determined by a portable scale preset for the container;

pouring in the order of 125 ml of a second premixed titration solvent from the first storage container up to a predetermined mark on the second container;

inserting a magnetic stirrer in the second container and positioning the second container on a magnetic stirrer base for providing agitation of the solution in the second container;

installing an electrode of a portable pH meter in the second container for measuring the pH of the solution in the second container;

pouring in the order of 25 ml of 0.1 N KOH alcoholic from a third storage container to a predetermined zero mark of a second burette;

titrating the solution in the second container with the second burette to raise the pH of the solution to in the order of 11 on the pH meter;

reading the second burette to determine the volume of 0.1 N KOH alcoholic used; and determining the Total Acid Number from the volume of 0.1 N KOH alcoholic used to determine the relative acid level of the lubrication oil.

11. The method as set forth in claim 1, including the steps of:

periodically determining the Total Base Number of the lubrication oil during the operation of the internal combustion engine using the aforementioned steps for predicting the change point for changing the lubricating oil.

12. An on-site method for protecting an internal combustion engine by precisely determining the change point for the lubricating oil of the engine in the field and for preventing damage to the engine, comprising the steps of:

determining the Total Base Number at the site in the field; and changing the lubrication oil when the Total Base Number has declined to a value of from about 1.0 to 0.5.

13. The method as set forth in claim 12, including the step of:

periodically determining the Total Base Number of the lubrication oil during operation of the internal combustion engine using the aforementioned steps for predicting the change point for changing the lubricating oil.

14. The method as set forth in claim 12, including the step of:

changing the lubrication oil when the Total Base Number has declined to a value of about 0.5.

15. An on-site method for protecting an internal combustion engine by precisely determining the change point for the lubricating oil of the engine in the field for maximum utilization of the oil and for preventing damage to the engine, consisting of the steps:

determining the Total Base Number at the site in the field; and changing the lubricating oil when the Total Base Number declines to a value of from about 1.0 to 0.5.

16. The method as set forth in claim 15, including the step of:

determining the Total Acid Number at the site in the field.

17. The method as set forth in claim 14, consisting of the step:

changing the lubrication oil when the Total Base Number has declined to a value of about 0.5.

* * * * *